US006833356B1

(12) United States Patent
Koenig et al.

(10) Patent No.: US 6,833,356 B1
(45) Date of Patent: Dec. 21, 2004

(54) PNEUMOCOCCAL PROTEIN HOMOLOGS AND FRAGMENTS FOR VACCINES

(75) Inventors: Scott Koenig, Rockville, MD (US); Jon Heinrichs, North Potomac, MD (US); Leslie S. Johnson, Germantown, MD (US); John E. Adamou, Germantown, MD (US)

(73) Assignee: Medimmune, Inc., Gaithersburg, MD (US)

( * ) Notice: Subject to any disclaimer, the term of this patent is extended or adjusted under 35 U.S.C. 154(b) by 197 days.

(21) Appl. No.: 09/645,835

(22) Filed: Aug. 25, 2000

Related U.S. Application Data

(60) Provisional application No. 60/150,750, filed on Aug. 25, 1999.

(51) Int. Cl.[7] .......................... C07K 14/00; A61K 38/16
(52) U.S. Cl. ............................. 514/12; 514/2; 530/350; 424/184.1; 424/130.1; 424/243.1; 424/244.1; 536/23.1
(58) Field of Search ................. 514/12, 2; 530/350, 530/23.1; 424/184.1, 130.1, 243.1, 244.1, 185.1; 536/23.1

(56) References Cited

U.S. PATENT DOCUMENTS 4,694,073 A * 9/1987 Bentle et al. ............... 530/399

2003/0031682 A1 * 2/2003 Brodeur et al. .......... 424/190.1

FOREIGN PATENT DOCUMENTS

| WO | WO 98/18930 | 5/1998 |
| WO | WO 99/42588 | 8/1999 |
| WO | WO 00/06736 | 2/2000 |

OTHER PUBLICATIONS

Spellerberg et al., Lmb, a protein with similarities to the Lral adhesin family, mediates attachment of streptococcus agalactiae to human laminin. Infection and Immunity Feb. 1999, vol. 67 871–878.*

* cited by examiner

*Primary Examiner*—Robert A. Wax
*Assistant Examiner*—Chih-Min Kam
(74) *Attorney, Agent, or Firm*—Elliott M. Olstein; Alan J. Grant

(57) ABSTRACT

The invention is directed to isolated polypeptides bearing sequence homology to the Sp36 protein found in pneumococcal organisms, such as *Streptococcus pneumoniae*. Polynucleotides encoding such polypeptides are also disclosed. The invention also relates to antibodies specific for the disclosed polypeptides and to uses of such antibodies in the treatment of diseases caused by staphylococci as well as group A and B streptococci. In addition, the invention relates to the use of the disclosed polypeptides in compositions and as vaccines and for prophylactic uses such as in vaccination of animals, especially humans, against a wide variety of streptococcal, staphylococcal and other diseases.

8 Claims, 9 Drawing Sheets

Figure 2(a)

```
                    10              20              30
 1   V K T Y G Y - I G S V A A I L L A T H I G S Y Q L G K H H   Gas36.pro
 1   V K T Y G Y - I G S V A A I L L A T H I G S Y Q L G K H H   Gbs36.PRO
 1   M K I N K K Y L V G S A A A L I L S - - V C S Y E L G L Y Q Pneumo Sp36.PRO 40              50              60
30   M G S A T K D N Q I A Y I D S K G K A K A P K T N K T M D   Gas36.pro
30   M G L A T K D N Q I A Y I D S K G K V K A P K T N K T M D   Gbs36.PRO
29   A R T V K E N N R V S Y I D G K Q A T Q K T - - E N L T P D Pneumo Sp36.PRO 70              80              90
60   Q I S A E E G I S A E Q I V V K I T D Q G Y V T S H G D H Y Gas36.pro
60   Q I S A E E G I S A E Q I V V K I T D Q G Y V T S H G D H Y Gbs36.PRO
57   E V S K R E G I N A E Q I V I K I T D Q G Y V T S H G D H Y Pneumo Sp36.PRO 100             110             120
90   H F Y N G K V P Y D A I I S E E L L M T D P N Y R F K Q S D Gas36.pro
90   H F Y N G K V P Y D A I I S E E L L M T D P N Y H F K Q S D Gbs36.PRO
87   H Y Y N G K V P Y D A I I S E E L L M K D P N Y K L K D E D Pneumo Sp36.PRO 130             140             150
120  V I N E I L D G Y V I K V N G N Y Y V Y L K P G S K R K N I Gas36.pro
120  V I N E I L D G Y V I K V N G N Y Y V Y L K P G S K R K N I Gbs36.PRO
117  I V N E V K G G Y V I K V D G K Y Y V Y L K D A A H A D N V Pneumo Sp36.PRO 160             170             180
150  R T K Q Q I A E Q V A K G T K E A K E K G L A Q V A H L S K Gas36.pro
150  R T K Q Q I A E Q V A K G T K E A K E K G L A Q V A H L S K Gbs36.PRO
147  R T K E E I N R Q - K Q E H S Q H R E G G T P R - - - - - - Pneumo Sp36.PRO 190             200             210
180  E E V A A V N E A K R Q G R Y T T D D G Y I F S P T D I I D Gas36.pro
180  E E V A A V N E A K R Q G R Y T T D D G Y I F S P T D I I D Gbs36.PRO
170  - N D G A V A L A R S Q G R Y T T D D G Y I F N A S D I I E Pneumo Sp36.PRO 220             230             240
210  D L G D A Y L V P H G N H Y H Y I P K D L S P S E L A A A   Gas36.pro
210  D L G D A Y L V P H G N H Y H Y I P K K D L S P S E L A A A Gbs36.PRO
199  D T G D A Y I V P H G D H Y H Y I P K N E L S A S E L A A A Pneumo Sp36.PRO 250             260             270
240  Q A Y W S Q K Q G R G A R P S D Y R P T P A P A P G R R K A Gas36.pro
240  Q A Y W S Q K Q G R G A R P S D Y R P T P A - - P G R R K A Gbs36.PRO
229  E A F L S G R - G N L S N S R T Y R R - Q N S D N T S R T N Pneumo Sp36.PRO 280             290             300
270  P I P D V T P N P G Q G H Q P D N G G Y H P A P P R P N D A Gas36.pro
268  P I P D V T P N P G Q G H Q P D N G G Y H P A P P R P N D A Gbs36.PRO
257  W V P S V S - - - - - - - - - - - - - N P G T T N T N T S   Pneumo Sp36.PRO 310             320             330
300  S Q N K H Q R D E F K G K T F K E L L D Q L H R L D L K Y R Gas36.pro
298  S Q N K H Q R D E F K G K T F K E L L D Q L H R L D L K Y R Gbs36.PRO
273  N N S N T N S Q A S Q S N D I D S L L K Q L Y K L P L S Q R Pneumo Sp36.PRO
```

Figure 2(b)

|     |           340           |           350           |           360           |             |
|-----|-------------------------|-------------------------|-------------------------|-------------|
| 330 | H V E E D G L I F E P T Q V I K S N A F G Y V V P H G D H Y | Gas36.pro |
| 328 | H V E E D G L I F E P T Q V I K S N A F G Y V V P H G D H Y | Gbs36.PRO |
| 303 | H V E S D G L V F D P A Q I T S R T A R G V A V P H G D H Y | Pneumo Sp36.PRO |

|     |           370           |           380           |           390           |             |
|-----|-------------------------|-------------------------|-------------------------|-------------|
| 360 | H I I P R S Q L S P L E M E L A D - - - R Y L A G Q - - -   | Gas36.pro |
| 358 | H I I P R S Q L S P L E M E L A D - - - R Y L A G Q - - -   | Gbs36.PRO |
| 333 | H F I P Y S Q M S E L E E R I A R I I P L R Y R S N H W V P | Pneumo Sp36.PRO |

|     |           400           |           410           |           420           |             |
|-----|-------------------------|-------------------------|-------------------------|-------------|
| 383 | T E D D D S G S D H S K P S D K E V T H T F L G H R I K A Y | Gas36.pro |
| 381 | T D D N D S G S D H S K P S D K E V T H T F L G H R I K A Y | Gbs36.PRO |
| 363 | D S R P E Q P S P Q P T P E P S P G P Q P A P N L K I D S N | Pneumo Sp36.PRO |

|     |           430           |           440           |           450           |             |
|-----|-------------------------|-------------------------|-------------------------|-------------|
| 413 | G K G L D G K P Y D T S D A Y V F S K E S I H S - V D K S G | Gas36.pro |
| 411 | G K G L D G K P Y D T S D A Y V F S K E S I H S - V D K S G | Gbs36.PRO |
| 393 | S S L V S Q L V R K V G E G Y V F E E K G I S R Y V F A K D | Pneumo Sp36.PRO |

|     |           460           |           470           |           480           |             |
|-----|-------------------------|-------------------------|-------------------------|-------------|
| 442 | V T A K H G D H F H Y - I G F G E L E Q Y E L D E V A N W V | Gas36.pro |
| 440 | V T A K H G D H F H Y - I G F G E L E Q Y E L D E V A N W V | Gbs36.PRO |
| 423 | L P S E T V K N L E S K L S K Q E S V S H T L T A K K E N V | Pneumo Sp36.PRO |

|     |           490           |           500           |           510           |             |
|-----|-------------------------|-------------------------|-------------------------|-------------|
| 471 | K A K G Q A - - D E L A A A L D Q E Q G K E K P L F D T K K | Gas36.pro |
| 469 | K A K G Q A - - D E L V A A L D Q E Q G K E K P L F D T K K | Gbs36.PRO |
| 453 | A P R D Q E F Y D K A Y N L L T E A H - - - K A L F E N K G | Pneumo Sp36.PRO |

|     |           520           |           530           |           540           |             |
|-----|-------------------------|-------------------------|-------------------------|-------------|
| 499 | V S R K V T K D G K V G Y M M P K D G K D Y F Y A R D Q L D | Gas36.pro |
| 497 | V S R K V T K D G K V G Y I M P K D G K D Y F Y A R Y Q L D | Gbs36.PRO |
| 480 | R N S D F Q A L D K L L E R L N D E S T N - - - - K E K L V | Pneumo Sp36.PRO |

|     |           550           |           560           |           570           |             |
|-----|-------------------------|-------------------------|-------------------------|-------------|
| 529 | L T Q I A F - - - - A E Q E L M L K D K K H Y R Y D I V D T | Gas36.pro |
| 527 | L T Q I A F - - - - A E Q E L M L K D K K H Y R Y D I V D T | Gbs36.PRO |
| 506 | D D L L A F L A P I T H P E R L G K P N S Q I E Y T E D E V | Pneumo Sp36.PRO |

|     |           580           |           590           |           600           |             |
|-----|-------------------------|-------------------------|-------------------------|-------------|
| 555 | G I E P R L A - - - V D V S S L P M H A G N A T Y D T G S S | Gas36.pro |
| 553 | G I E P R L A - - - V D V S S L P M H A G N A T Y D T G S S | Gbs36.PRO |
| 536 | R I - A Q L A D K Y T T S D G Y I F D E H Q I I S D E G D A | Pneumo Sp36.PRO |

|     |           610           |           620           |           630           |             |
|-----|-------------------------|-------------------------|-------------------------|-------------|
| 582 | F V I P H I D H I H V V P Y S W L T - R D Q I A T I K Y V M | Gas36.pro |
| 580 | F V I P H I D H I H V V P Y S W L T - R N Q I A T I K Y V M | Gbs36.PRO |
| 565 | Y V T P H M G H S H W I G K D S L S D K E K V A A Q A Y T K | Pneumo Sp36.PRO |

|     |           640           |           650           |           660           |             |
|-----|-------------------------|-------------------------|-------------------------|-------------|
| 611 | Q H P E V R P - - - - D I W S K P G H E E S G S V I P N V T | Gas36.pro |
| 609 | Q H P E V R P - - - - D V W S K P G H E E S G S V I P N V T | Gbs36.PRO |
| 595 | E K G I L P P S P D A D V K A N P T G Q S A A A I Y N R V K | Pneumo Sp36.PRO |

Figure 2(c)

```
              670                    680                    690
637  P L D K R A G M P N W Q - I I H S A E E V Q K A L A E G R F   Gas36.pro
635  P L D K R A G M P N W Q - I I H S A E E V Q K A L A E G R F   Gbs36.PRO
625  G - E K R I P L V R L P Y M V E H T V E V K N G - - - - - -   Pneumo Sp36.PRO 700                    710                    720
666  A T P D G Y I F D P R D V L A K E T F V W - K D G S F S I P   Gas36.pro
664  A A P D G Y I F D P R D V L A K E T F V W - K D G S F S I P   Gbs36.PRO
648  - - - - N L I I P H K D H Y H N I K F A W F D D H T Y K A P   Pneumo Sp36.PRO 730                    740                    750
695  R A D G S S L R T I - - - - - - - - - N K S D L S Q A E       Gas36.pro
693  R A D G S S L R T I - - - - - - - - - N K S D L S Q A E       Gbs36.PRO
674  - - N G Y T L E D L F A T I K Y Y V E H P D E R P H S N D G   Pneumo Sp36.PRO 760                    770                    780
714  W Q Q A Q E - L L A K K N A G D A T D T D - K P K E K Q Q A   Gas36.pro
712  W Q Q A Q E - L L A K K N A G D A T D T D - K P E E K Q Q A   Gbs36.PRO
702  W G N A S E H V L G K K D H S E D P N K N F K A D E E P V E   Pneumo Sp36.PRO 790                    800                    810
742  D K S N E N Q Q P - - - S E A S K E E E K E S D D F I D S L   Gas36.pro
740  D K S N E N Q Q P - - - S E A S K E E - K E S D D F I D S L   Gbs36.PRO
732  E T P A E P E V P Q V E T E K V E A Q L K E A E V L L A K V   Pneumo Sp36.PRO 820                    830                    840
769  P D Y G L D R A T L E D H I N Q L A Q K A N I D P K Y L I F   Gas36.pro
766  P D Y G L D R A T L E D H I N Q L A Q K A N I D P K Y L I F   Gbs36.PRO
762  T D S S L - K A N A T E T L A G L R N N L T L Q - - - L M     Pneumo Sp36.PRO 850                    860                    870
799  Q P E G V Q F Y N K N G E L V T Y - - - - Q I K T L Q Q I N   Gas36.pro
796  Q P E G V Q F Y N K N G E L V T Y - - - - Q I K T L Q Q I N   Gbs36.PRO
787  D N N S I M - - A E A E K L L A L L K G S N P S S V S K E K   Pneumo Sp36.PRO 825  P                                                             Gas36.pro
822  P                                                             Gbs36.PRO
815  L N                                                           Pneumo Sp36.PRO
```

Control
Sp36 GBS
Sp36
SJ2 6b

Figure 5A

```
VKKTYGYIGS VAAILLATHI GSYQLGKHHM GSATKDNQIA YIDDSKGKAK APKTNKTMDQ ISAEEGISAE   70
QIVVKITDQG YVTSHGDHYH FYNGKVPYDA IISEBLLMTD PNYRFKQSDV INEILDGYVI KVNGNYYVYL  140
KPGSKRKNIR TKQQIAEQVA KGTKEAKEKG LAQVAHLSKE EVAAVNEAKR QGRYTTDDGY IFSPTDIIDD  210
LGDAYLVPHG NHYHYIPKKD LSPSELAAAQ AYWSQKQGRG ARPSDYRPTP APAPGRRKAP IPDVTPNPGQ  280
GHQPDNGGYH PAPPRPNDAS QNKHQRDEFK GKTFKELLDQ LHRLDLKYRH VEEDGLIFEP TQVIKSNAFG  350
YVVPHGDHYH IIPRSQLSPL EMELADRYLA GQTEDDDSGS DHSKPSDKEV THTFLGHRIK AYGKGLDGKP  420
YDTSDAYVFS KESIHSVDKS GVTAKHGDHF HYIGFGELEQ YELDEVANWV KAKGQADELA AALDQEQGKE  490
KPLFDTKKVS RKVTKDGKVG YMMPKDGKDY FYARDQLDLT QIAFAEQELM LKDKKHYRYD IVDTGIEPRL  560
AVDVSSLPMH AGNATYDTGS SFVIPHIDHI HVVPYSWLTR DQIATIKYVM QHPEVRPDIW SKPGHEESGS  630
VIPNVTPLDK RAGMPNWQII HSAEEVQKAL AEGRFATPDG YIFDPRDVLA KETFVWKDGS FSIPRADGSS  700
LRTINKSDLS QAEWQQAQEL LAKKNAGDAT DTDKPKEKQQ ADKSNENQQP SEASKEEEKE SDDFIDSLPD  770
YGLDRATLED HINQLAQKAN IDPKYLIFQP EGVQFYNKNG ELVTYDIKTL QQINP                 825
```

Figure 5B

```
MKTKKVIILV GLLLSSQLTL IACQSRGNGT YPIKTKQSRK GMTSNKIKPI KKSKKTNKTH KGVAGVDFPT  70
DDGFILTKDS KILSKTDQGI VVDHDGHSHF IFYADLKGSP FEYLIPKGAS LAKPAVAQRA ASQGTSKVAD 140
PHHHYEFNPA DIVAEDALGY TVRHDDHFHY ILKSSLSGQT QAQAKQVATR LPQTSSLVST ATANGIPGLH 210
FPTSDGFQFN GQGIVGVTKD SILVDHDGHL HPISFADLRQ GGWAHVADQY DPAKKAEKPA ETHQTPELSE 280
REKEYQEKLA YLAEKLGIDP STIKRVETQD GKLGLEYPHH DHAHVLMLSD IEIGKDIPDP HAIEHARELE 350
KHKVGMDTLR ALGFDEEVIL DIVRTHDAPT PFPSNEKDPN MMKEWLATVI KLDLGSRKDP LQRKGLSLLP 420
NLETLGIGFT PIKDISPVLQ FKKLKQLLMT KTGVTDYRFL DNMPQLEGID ISQNNLKDIS FLSKYKNLTL 490
VAAADNGIED IRPLGQLPNL KFLVLSNNKI SDLSPLASLH QLQELHIDNN QITDLSPVSH KESLTVVDLS 560
RNADVDLATL QAPKLETLMV NDTKVSHLDF LKNNPNLSSL SINRAQLQSL EGIEASSVIV RVEAEGNQIK 630
SLVLKDKQGS LTFLDVTGNQ LTSLEGVNNF TALDILSVSK NQLTNVNLSK PNKTVTNIDI SHNNISLADL 700
KLNEQHIPEA IAKNFPAVYE GSMVGNGTAE EKAAMATKAK ESAQEASESH DYNHNHTYED EEGHAHEHRD 770
KDDHDHEHED ENEAKDEQNH AD                                                   792
```

Figure 5C

```
VKKTYGYIGS VAAILLATHI GSYQLGKHHM GLATKDNQIA YIDDSKGKVK APKTNKTMDQ ISAEEGISAE  70
QIVVKITDQG YVTSHGDHYH FYNGKVPYDA IISEELLMTD PNYHFKQSDV INEILDGYVI KVNGNYYVYL 140
KPGSKRKNIR TKQQIAEQVA KGTKEAKEKG LAQVAHLSKE EVAAVNEAKR QGRYTTDDGY IFSPTDIIDD 210
LGDAYLVPHG NHYHYIPKKD LSPSELAAAQ AYWSQKQGRG ARPSDYRPTP APGRRKAPIP DVTPNPGQGH 280
QPDNGGYHPA PPRPNDASQN KHQRDEFKGK TFKELLDQLH RLDLKYRHVE EDGLIFEPTQ VIKSNAFGYV 350
VPHGDHYHII PRSQLSPLEM ELADRYLAGQ TDDNDSGSDH SKPSDKEVTH TFLGHRIKAY GKGLDGKPYD 420
TSDAYVFSKE SIHSVDKSGV TAKHGDHFHY IGFGELEQYE LDEVANWVKA KGQADELVAA LDQEQGKEKP 490
LFDTKKVSRK VTKDGKVGYI MPKDGKDYFY ARYQLDLTQI AFAEQELMLK DKKHYRYDIV DTGIEPRLAV 560
DVSSLPMHAG NATYDTGSSF VIPHIDHIHV VPYSWLTRNQ IATIKYVMQH PEVRPDVWSK PGHEESGSVI 630
PNVTPLDKRA GMPNWQIIHS AEEVQKALAE GRFAAPDGYI FDPRDVLAKE TFVWKDGSFS IPRADGSSLR 700
TINKSDLSQA EWQQAQELLA KKNAGDATDT DKPEEKQQAD KSNENQQPSE ASKEEKESDD FIDSLPDYGL 770
DRATLEDHIN QLAQKANIDP KYLIFQPEGV QFYNKNGELV TYDIKTLQQI NP                   822
```

PNEUMOCOCCAL PROTEIN HOMOLOGS AND FRAGMENTS FOR VACCINES

This application claims the priority of U.S. Provisional Application No. 60/150,750, filed Aug. 25, 1999, the disclosure of which is hereby incorporated by reference in its entirety.

FIELD OF THE INVENTION

This invention relates generally to the field of bacterial antigens and their use, for example, as immunogenic agents in humans and animals to stimulate an immune response. More specifically, it relates to the vaccination of mammalian species, especially humans, with one or more polypeptides derived from gram positive bacteria and which show sequence homology with an immunogenic polypeptide obtained from Streptococcus pneumoniae.

BACKGROUND OF THE INVENTION

Polypeptides derived from gram positive bacteria are useful for stimulating production of antibodies that protect the vaccine recipient against infection by a wide range of serotypes of pathogenic gram positive bacteria, including *S. pneumoniae*. Further, the invention relates to antibodies against such polypeptides useful in diagnosis and passive immune therapy with respect to diagnosing and treating such pneumococcal infections.

The genus Streptococcus contains a variety of species responsible for causing disease in mammals, including humans, while also encompassing species that constitute normal flora in humans and other mammals. Among the bacterial species implicated in the etiology of diseases in humans are *S. pyogenes* (part of the group A streptococcal bacteria, herein designated "GAS" for "group A streptococci"), *S. pneumoniae* (referred to as "pneumococcus") and *S. agalactiae* (the group B streptococci or "GBS"). The group A streptococci cause serious diseases such as necrotizing fasciitis, scarlet fever and sepsis, as well as less virulent diseases such as impetigo and pharyngitis. The pneumococci are the most common cause of community-acquired pneumonia and are also responsible for more than half of all cases of otitis media in children. The pneumococci are also the second most common pathogen associated with bacterial meningitis. The group B streptococci are the most prevalent pathogen associated with illness and death among newborns in the United States.

Currently, there are no vaccines available for the prevention of diseases caused by the group A and group B streptococci and presently available pneumococcal vaccines are not effective in children under 2 years of age or in the elderly due to the poor immunogenicity of the capsular carbohydrates that compose the current vaccine. It would therefore be highly advantageous to produce a vaccine that would prevent infection by these classes of pathogen, especially in the age groups mentioned.

In addition to the pathogens just described, some bacteria of the genus Staphylococcus are also of clinical importance. In fact, two of these are among the leading causes of nosocomial infections (infections acquired while in the hospital). Both *Staphylococcus aureus* and *Staphylococcus epidermidis* readily colonize the skin of healthy individuals and can cause acute disease in patients following immunosuppression or traumatic injury. Infections caused by these species include bacteremia, endocarditis, osteomyelitis, wound infections and infections associated with indwelling catheters.

*Streptococcus pneumoniae* is a gram positive bacterium that is a major causative agent in invasive infections in animals and humans, such as the aforementioned sepsis, meningitis, and otitis media, as well as lobar pneumonia (Tuomanen, et al. *New England J. of Medicine* 322:1280–1284 (1995)). As part of the infection process, pneumococci readily bind to non-inflamed human epithelial cells of the upper and lower respiratory tract by binding to eukaryotic carbohydrates in a lectin-like manner (Cundell et al., *Micro. Path.* 17:361–374 (1994)). Conversion to invasive pneumococcal infections for bound bacteria may involve the local generation of inflammatory factors which may activate the epithelial cells to change the number and type of receptors on their surface (Cundell, et al., *Nature*, 377:435–438 (1995)). Apparently, one such receptor, platelet activating factor (PAF) is engaged by the pneumococcal bacteria and within a very short period of time (minutes) from the appearance of PAF, pneumococci exhibit strongly enhanced adherence and invasion of tissue. Certain soluble receptor analogs have been shown to prevent the progression of pneumococcal infections (Idanpaan-Heikkila et al., *J. Inf. Dis.*, 176:704–712 (1997)). A number of other proteins have been suggested as being involved in the pathogenicity of *S. pneumoniae*.

*Streptococcus pneumoniae* itself has been shown to contain a gene which encodes a protein designated herein as Sp36. This protein has a predicted molecular mass of 91,538 Da and contains 5 histidine triad motifs (proposed to be involved in metal binding). The gene encoding this protein appears to be present the 23 serotypes comprising the current commercially available pneumococcal-capsular vaccine. Immunization of mice with this protein, in the presence of Freund's adjuvant, stimulates an immune response which protects these mice from an intraperitoneal challenge with a dose of virulent pneumococci that would normally kill the mice.

For the reasons already stated above, there not only remains a need for identifying polypeptides having epitopes in common from various strains of *S. pneumoniae* but also from a broader spectrum of gram positive bacteria in order to utilize such polypeptides as vaccines to provide protection against a wide variety of infectious organisms.

BRIEF SUMMARY OF THE INVENTION

In accordance with the present invention, there is provided vaccines that include polypeptides obtained from gram positive bacteria other than *S. pneumoniae*, as well as variants of said polypeptides and active fragments of such polypeptides.

The present invention is also directed to novel genes, and the polypeptides encoded thereby, derived from gram positive bacteria other than *S. pneumoniae*, and which bear sequence homology to the Sp36 gene already described. Such gram positive bacteria include the group A and B streptococci, as described herein, as well as species of the genus Staphylococcus, especially *S. aureus*.

In a particular embodiment, the present invention is directed to specific gene sequences, and proteins encoded thereby, derived from the group A and group B streptococci, and to the use of such expressed polypeptides and proteins as the basis for pharmaceutical compositions useful as vaccines and as a means for enabling isolation of antibodies with therapeutic and/or prophylactic activity (such as would be useful in preparing products like CytoGam).

In a further embodiment, the present invention also relates to the preparation and use of fragments of the novel polypeptides disclosed herein, such fragments being immunogenic in nature and being useful in the preparation of vaccines against diseases caused by the pathogens from which such polypeptides, and fragments thereof, are derived.

BRIEF DESCRIPTION OF DRAWINGS

FIG. 2 shows an alignment between the Sp36 amino acid sequence from S. pneumoniae strain N4 (SEQ ID NO: 7) and the homologous sequences from S. pyogenes (SEQ ID NO: 2) and S. agalactiae (SEQ ID NO: 6). Amino acids identical to those of the polypeptide from S. pneumoniae are boxed.

FIGS. 5A–5C show the amino acid sequence for the GAS36 homologs with the histidine triad regions underlined (FIGS. 5A and 5B) and the sequence for a GBS36 homolog (FIG. 5C) with its histidine triad regions underlined.

DETAILED DESCRIPTION OF THE INVENTION

Figure 1:
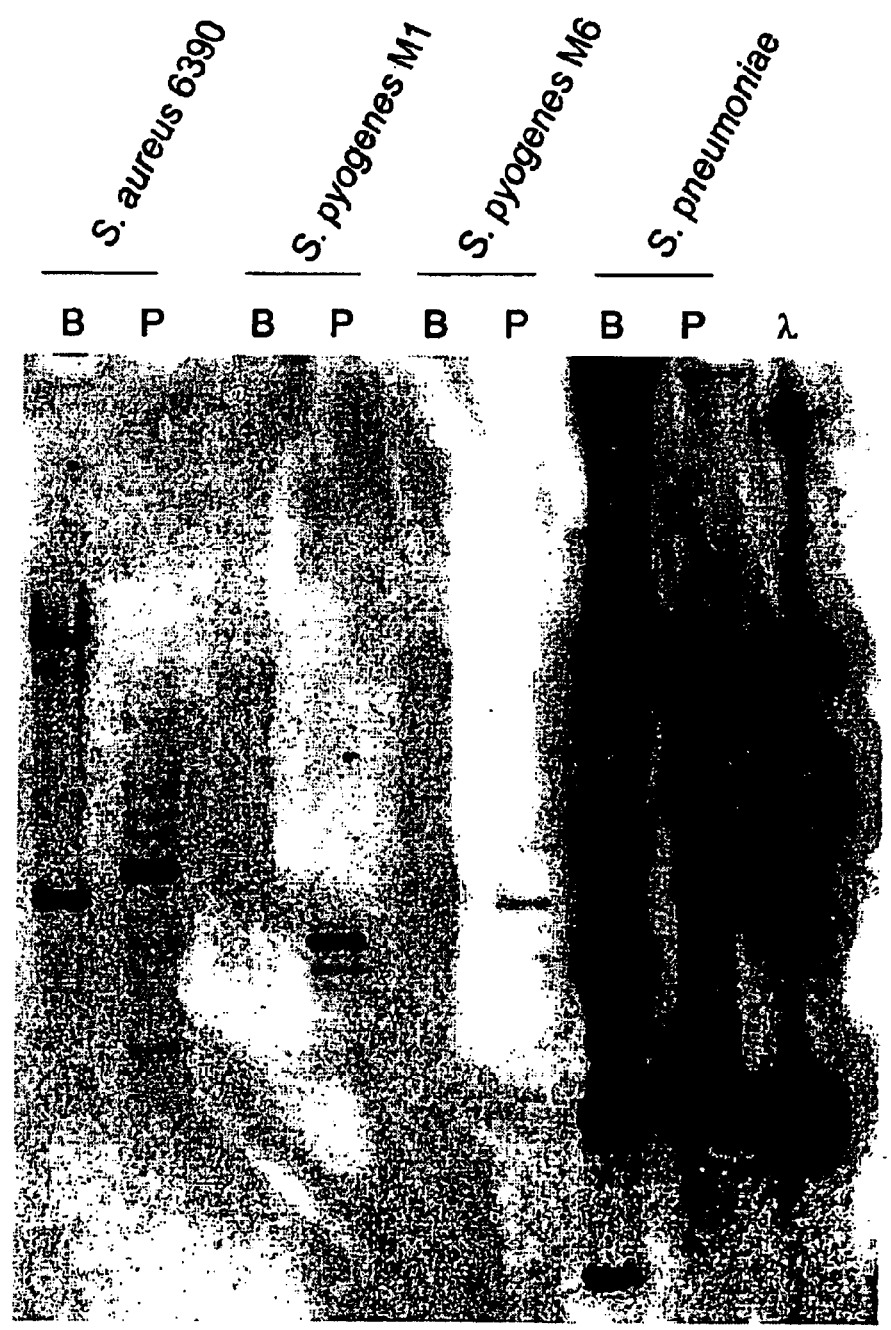
FIG. 1 shows the results of a Southern blot of genomic DNA from S. aureus, S. pyogenes, and pneumococcus. The DNA was digested with restriction nucleases BamHI or PvuII, and after electrophoresis and transfer to a nylon membrane, was probed with a labeled DNA fragment encompassing the pneumococcal gene encoding Sp36. The hybridization and washes were carried out under low stringency conditions. The results show hybridization by the labeled probe to a S. aureus fragment in both the BamHI and PvuII lanes and to two fragments in the PvuII digests of two strains of S. pyogenes.
Figure 3:
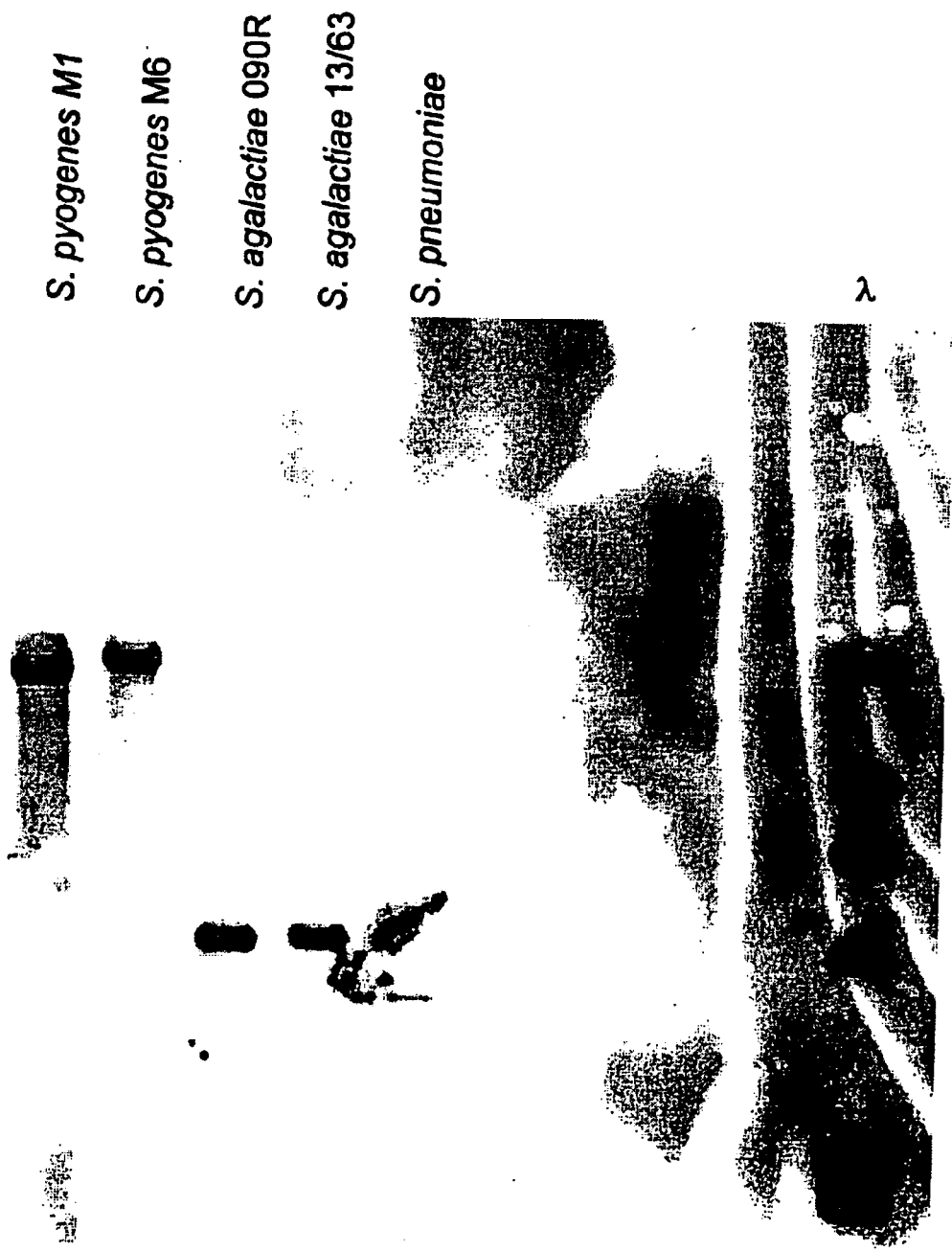
FIG. 3 shows the results of a Southern blot of genomic DNA from S. pyogenes, S. agalactiae, and S. pneumoniae probed with DNA encoding the full length Sp36 homolog from S. pyogenes. The hybridization was carried out under low stringency conditions. These results demonstrate that the S. pyogenes Sp36 homolog, used as a probe, is capable of detecting a homologous gene in S. agalactiae and pneumococcus.
Figure 4:
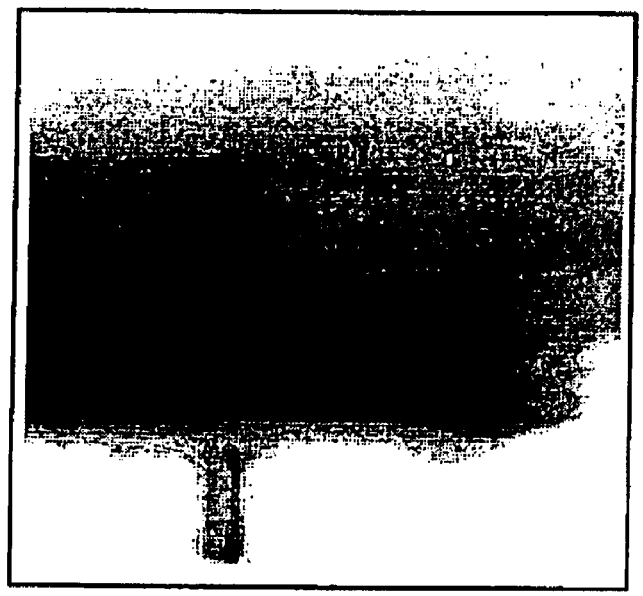
FIG. 4 shows the results of a western blot using rabbit polyclonal antiserum generated against recombinant Sp36 protein cloned from S. pneumoniae strain Norway 4. The results demonstrate that this antiserum not only reacts with the protein against which it was raised (here, Sp36), as well as to a protein of similar size in a lysate of a serotype 6B strain of pneumococcus, but also reacts with a recombinant protein encoded by the Sp36 homolog gene of group B streptococci.

The present invention is directed to novel polynucleotides and polypeptides derived from species of gram positive bacteria, especially group A and B streptococci, and including the genus Staphylococcus, most especially S. pyogenes (GAS), S. agalactiae (GBS), and S. aureus, respectively.

Further, the present invention is directed to polynucleotides derived from gram positive bacteria and which are at least partially homologous to the polynucleotides making up the gene coding for the previously disclosed Sp36 gene of S. pneumoniae (U.S. application Ser. No. 60/113,048).

The present invention is also directed to polynucleotides, and immunologically active fragments, segments, or portions, thereof, which polypeptides are encoded by the polynucleotides disclosed herein.

The present invention also relates to such polynucleotides and polypeptides in enriched, preferably isolated, or even purified, form.

In accordance with the present invention, the term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where they do not interfere with manipulation or expression of the coding regions.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

"Isolated" in the context of the present invention with respect to polypeptides (or polynucleotides) means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and most preferably are purified to homogeneity.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptides having a purity of preferably 0.001%, or at least 0.01% or 0.1%; and even 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological function or activity as the expression product of the complete coding region.

The term "primer" means a short nucleic acid sequence that is paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100 $[1-(C/R)]$ wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

Thus, the present invention is directed to novel, isolated polypeptides comprising an amino acid sequence at least 75% identical to a sequence in SEQ ID NO: 2, 4 or 6, preferably polypeptides at least 90% identical thereto, more preferably 95% identical to the sequence of SEQ ID NO: 2 or 4, and most preferably having the sequence of either SEQ ID NO: 2 or 4.

The isolated polypeptides of the present invention may be found in a wide variety of microorganisms, but will commonly be found in an organism selected from the group consisting of group A streptococci, group B streptococci, and *Staphylococcus aureus*, and wherein the group A streptococcal organism is *Streptococcus pyogenes* and the group B streptococcal organism is *Streptococcus agalactiae*. Also, polypeptides of the invention include, but are in no way limited to, isolated polypeptides having a sequence at least 25% identical to the amino acid sequence of the Sp36 protein of *Streptococcus pneumoniae*.

The present invention further relates to immunogenically active fragments of the isolated polypeptides disclosed herein.

The terms "fragment," "derivative" and "analog" when referring to the polypeptides disclosed herein means a polypeptide which retains essentially the same biological function or activity as such polypeptide. Thus, an analog includes a proprotein, or preprotein, which can be activated by cleavage of the proprotein portion to produce an active mature polypeptide. Such fragments, derivatives and analogs must have sufficient similarity to the polypeptide of SEQ ID NO:2, 4 or 6 so that immunogenic activity of the native polypeptide is retained.

The polypeptide of the present invention may be a recombinant polypeptide, a natural polypeptide or a synthetic polypeptide, preferably a recombinant polypeptide.

The fragment, derivative or analog of the polypeptide of SEQ ID NO:2, 4, or 6 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

As used herein with reference to polypeptides, the terms "portion," "segment," and "fragment," refer also to a continuous sequence of residues, such as amino acid residues, which sequence forms a subset of a larger sequence. For example, if a polypeptide were subjected to treatment with any of the common endopeptidases, such as trypsin, chymotrypsin, or papain, the oligopeptides resulting from such treatment would represent portions, segments or fragments of the starting polypeptide.

The present invention is also directed to isolated polynucleotides whose sequences contain coding regions encoding the polypeptides of the present invention, preferably the polypeptides of SEQ ID NO: 2, 4, and 6 and most preferably will be the isolated polynucleotides comprising the sequences of SEQ ID NOS: 1, 3, and 5.

The present invention is also directed to fragments or portions of such sequences which contain at least 15 bases, preferably at least 30 bases, more preferably at least 50 bases and most preferably at least 80 bases, and to those sequences which are at least 60%, preferably at least 80%, and most preferably at least 95%, especially 98%, identical thereto, and to DNA (or RNA) sequences encoding the same polypeptide as the sequences of SEQ ID NOS: 2, 4, and 6, including fragments and portions thereof and, when derived from natural sources, includes alleles thereof.

Yet another aspect of the present invention is directed to an isolated DNA (or RNA) sequence or molecule comprising at least the coding region of a bacterial gene (or a DNA sequence encoding the same polypeptide as such coding region), in particular an expressed bacterial gene, which bacterial gene comprises a DNA sequence homologous with, or contributing to, the sequence depicted in SEQ ID NOS: 1, 3, and 5 or one at least 60%, preferably at least 80%, and most preferably at least 95%, especially 98%, identical thereto, including 100% identity, as well as fragments or portions of the coding region which encode a polypeptide having a similar function to the polypeptide encoded by said coding region. Thus, the isolated DNA (or RNA) sequence may include only the coding region of the expressed gene (or fragment or portion thereof as hereinabove indicated) or may further include all or a portion of the non-coding DNA (or RNA) of the expressed bacterial gene.

In general, sequences homologous with and contributing to the sequences of SEQ ID NOS: 1, 3, and 5 (or one at least 60%, preferably at least 80%, and most preferably at least 95% identical or homologous thereto) are from the coding region of a bacterial gene.

The polynucleotides according to the present invention may also occur in the form of mixtures of polynucleotides hybridizable to some extent with the gene sequences containing any of the nucleotide sequences of SEQ ID NOS: 1, 3, and 5, including any and all fragments thereof, and which polynucleotide mixtures may be composed of any number of such polynucleotides, or fragments thereof, including mixtures having at least 10, perhaps at least 30 such sequences, or fragments thereof.

Fragments of the full length polynucleotide of the present invention may be used as hybridization probes for a DNA library to isolate the full length DNA and to isolate other DNAs which have a high sequence similarity to the gene or similar biological activity. Probes of this type preferably have at least 15 bases, may have at least 30 bases and even 50 or more bases. The probe may also be used to identify a DNA clone corresponding to a full length transcript and a genomic clone or clones that contain the complete gene including regulatory and promotor regions. An example of a screen comprises isolating the coding region of the gene by using the known DNA sequence to synthesize an oligonucleotide probe. Labeled oligonucleotides having a sequence complementary to that of the gene of the present invention are used to screen a library of DNA or mRNA to determine which members of the library the probe hybridizes to.

The present invention is also directed to vectors comprising the polynucleotides disclosed herein, as well as to genetically engineered cells comprising such vectors and/or polynucleotides. Thus, the present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequencers) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma;

adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, phiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference, Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polypeptides of the present invention, when utilized for clinically related purposes, may also be suspended in a pharmacologically acceptable diluent or excipient to facilitate such uses, which will include use as a vaccine for the purpose of preventing a wide variety of streptococcal and staphylococcal infections.

In accordance with another aspect of the present invention, there is provided a vaccine that includes at least one polypeptide that is at least 75% identical, preferably at least 90% identical and most preferably 95% identical, to a polypeptide sequence comprising the sequence of SEQ ID NO: 2, 4, or 6. Such variations in homology for putative vaccines are well known in the art (See, for example, Hanson et al., "Active and Passive Immunity Against Borrelia burgdorferi Decorin Binding Protein A (DbpA)," *Infection and Immunity*, (May) 1998, p. 2143–2153; Roberts et al., "Heterogeneity Among Genes Including Decorin Binding Proteins A and B of Borrelia burgdorferi sensu lato," *Infection and Immunity*, (November) 1998, p. 5275–5285). Such observations would similarly apply to portions, segments or fragments of the polypeptides disclosed herein.

Such segments find a multitude of uses. For example, such segments of the polypeptides according to the present invention find use as intermediates in the synthesis of higher molecular weight structures also within the present invention.

The term "active fragment" means a fragment that generates an immune response (i.e., has immunogenic activity) when administered, alone or optionally with a suitable adjuvant, to an animal, such as a mammal, for example, a rabbit or a mouse, and also including a human.

In accordance with a further aspect of the invention, a vaccine of the type hereinabove described is administered for the purpose of preventing or treating infection caused by streptococci and staphylococci as well as many related organisms.

A vaccine in accordance with the present invention may include one or more of the hereinabove described polypeptides or active fragments thereof. When employing more than one polypeptide or active fragment, such as two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

In many cases, the variation in the polypeptide or active fragment is a conservative amino acid substitution, although other substitutions are within the scope of the invention.

In accordance with the present invention, a polypeptide variant includes variants in which one or more amino acids are substituted and/or deleted and/or inserted.

In another aspect, the invention relates to passive immunity vaccines formulated from antibodies against a polypeptide or active fragment of a polypeptide of the present invention. Such passive immunity vaccines can be utilized to prevent and/or treat streptococcal and staphylococcal infections in patients. In this manner, according to a further aspect of the invention, a vaccine can be produced from a synthetic or recombinant polypeptide of the present invention or an antibody against such polypeptide.

Still another aspect the present invention relates to a method of using one or more antibodies (monoclonal, polyclonal or sera) to the polypeptides of the invention as described above for the prophylaxis and/or treatment of diseases that are caused by streptococcal and staphylococcal bacteria. In particular, the invention relates to a method for the prophylaxis and/or treatment of infectious diseases that are caused by streptococci and staphylococci. In a still further preferred aspect, the invention relates to a method for the prophylaxis and/or treatment of such diseases as necrotizing fasciitis, scarlet fever, sepsis and many diseases of newborns, in humans by utilizing a vaccine of the present invention.

Generally, vaccines are prepared as injectables, in the form of aqueous solutions or suspensions. Vaccines in an oil base are also well known such as for inhaling. Solid forms which ate dissolved or suspended prior to use may also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 0.5 to 500 $\mu$g purified protein may be given.

The present invention is also directed to a vaccine in which a polypeptide or active fragment of the present invention is delivered or administered in the form of a polynucleotide encoding the polypeptide or active fragment, whereby the polypeptide or active fragment is produced in vivo. The polynucleotide may be included in a suitable expression vector and combined with a pharmaceutically acceptable carrier.

Thus, the present invention expressly contemplates a vaccine composition comprising any of the polypeptides disclosed herein, said polypeptide being present in an amount effective to produce an immune response and wherein said polypeptide is suspended in a pharmacologically acceptable carrier, diluent or excipient.

The vaccine compositions of the present invention may also comprise live vaccines, containing such organisms as *Steptococcus gordoniae* and *Salmonella typhi*, wherein said organisms contain recombinant polypeptides as disclosed herein.

In addition, the polypeptides of the present invention can be used as immunogens to stimulate the production of antibodies for use in passive immunotherapy, for use as diagnostic reagents, and for use as reagents in other processes such as affinity chromatography.

Thus, the present invention is also directed to method s for the prevention of a wide variety o f diseases caused by streptococcal and staphylococcal organisms, said methods involving the administering of vaccines disclosed herein to animals at risk of such diseases, especially where said animals are humans.

In addition, the invention disclosed herein is also directed to a means of treating animals, especially humans, afflicted with a disease caused by the organisms from which the isolated polypeptides of the invention are derived, such methods including, but not being limited to, administering to an animal, especially a human, afflicted with such a disease of a therapeutically effective amount of an antibody, or mixture of antibodies, against the polypeptides disclosed herein.

Antibodies specific for the polypeptides disclosed herein may be either polyclonal or monoclonal and may even be in the form of antisera. When such antibodies are monoclonal in nature, they may be produced by conventional methods of preparing monoclonal antibodies, such as from conventional hybridoma cells, and may also be produced by genetically engineered cells transformed with vectors containing genes specifically coding for the different heavy and light chains of antibody molecules having an arrangement of variable regions specifically complementary to one or more of the polypeptides of the invention. Such recombinantly produced antibodies may be in the form of either dimers or tetramers, depending on the type of cellular expression system utilized therefor.

The invention will now be further described in more detail in the following non-limiting examples and it will be appreciated that additional and different embodiments of the teachings of the present invention will doubtless suggest themselves to those of skill in the art and such other embodiments are considered to have been inferred from the disclosure herein.

EXAMPLE 1

Southern Blot Analysis of Chromosomal DNA using Probes Specific for the Sp36 Gene of *Streptococcus pneumonias*

Genomic DNA was isolated from *Staphylococcus aureus, Streptococcus pyogenes* (group A), and Streptococcus agalactiae (group B) after overnight growth of the bacteria. The DNA was digested to completion by overnight incubation with restriction enzymes (BamHI and PvuII), and then DNA fragments were resolved by size by agarose gel electrophoresis before transfer to a nylon membrane. The membrane was then probed with DNA encoding the entire Sp36 open reading frame that had been fluorescein-labeled with random primers using a kit from Amersham Pharmacia Biotech Inc. The hybridization and washes were carried out under low stringency conditions (i.e., 45° C., 5×SSC hybridization; 45° C., 1×SSC for $1^{st}$ wash; 45° C., 0.5×SSC for $2^{nd}$ wash). Here, SSC is composed of 150 mM NaCl and 15 nM sodium citrate, pH 7.0 and all washes are 50 mL each.

After hybridization and washing was complete, the bound, fluorescein-labeled probe was detected using an anti-fluorescein antibody as per the manufacturer's instructions with the kit. Similarly digested DNA from *Streptococcus pneumoniae* strain SJ2 (serotype 6B) was used as a positive control. Fluorescein-labeled bacteriophage lambda DNA digested with the restriction nuclease HindIII was used as a size marker.

The Sp36 probe hybridized with a single fragment in the digested *S. aureus* DNA (~4.5 kb BamHI fragment, ~5 kb PvuII fragment) and with 2 major fragments in a PvuII digest of serotype M1 of the group A streptococci genomic DNA (~4.0 kb, and ~4.2 kb).

EXAMPLE 2

BLAST Analysis using Sp36 Predicted Amino Acid Sequence

Sequence comparisons of the Sp36 encoded protein sequence against the publicly available GenBank sequence database (including the unfinished microbial database) revealed two highly homologous amino acid sequences. One of these was a predicted amino acid sequence from the *S. pyogenes* genome. This predicted polypeptde comprised 825 amino acid residues (MW=92,616 Da) that was 25.1% identical to the Sp36 amino acid sequence from pneumococcus serotype 4 but maintained the 5 histidine triads (underlined in FIG. 5A —SEQ ID NO: 2). The second polypeptide encoded within the *S. pyogenes* database contained several errors that were corrected by our sequencing of this region of the genome. The DNA fragment obtained encoded a protein of 792 amino acids (MW=87,457 Da) that was 12.6% identical to the pneumococcal sequence and 12.5% identical to the first *S. pyogenes* polypeptide. This predicted amino acid sequence contained four histidine triad motifs (underlined in FIG. 5B —SEQ ID NO.: 4). The third polypeptide sequence obtained was one already in the database (Accession No. AF062533) and identified only as an unknown gene downstream from a gene identified as Imb in *S. galactiae*. This 822 amino acid protein thus has a predicted molecular weight of 92,353 Da and maintains the 5 histidine triad motifs (underlined in FIG. 5C —SEQ ID NO: 6). This second polypeptide shows 25.6% sequence identity to Sp36 of pneumococcus type 4 and 97.7% and 11.6% identity to the two group A homologs, respectively.

EXAMPLE 3

Southern Blot Analysis using a group A Streptococcal Sp36 Homolog Probe

Southern blot analysis was performed with a fluorescein-labeled DNA fragment as probe, which encoding a group A streptococcal Sp36 homolog cloned from an M1 serotype of the group A streptococcal genome. This fragment was then used to probe genomic DNA from an M6 serotype of the group A streptococcal genome, as well as serotype 1a and serotype 3 of the group B streptococcal genome, and strain SJ2 (serotype 6B) of pneumococcus. In all cases, a single band was obtained in DNA digested with BamHI when hybridization was carried out under low stringency conditions (as described above). A band of about 20 kb was visualized in group A streptococcal DNA, about 4.5 kb was obtained for group B streptococcal DNA, and a band of about 4 kb was seen for pneumococcus.

EXAMPLE 4

Western Blot Analysis of Reactivity of group B Streptococcal Homolog with Anti-pneumococcal Sp36 Antiserum To determine whether antiserum raised against recombinant Sp36 from *S. pneumoniae* would recognize the recombinant Sp36 homolog encoded by group B streptococcal organisms, a western blot was performed. One hundred nanograms (100 ng) of recombinant Sp36 polypeptide cloned from either *S. pneumoniae* serotype 4, or of the Sp36 homolog cloned from group B streptococcal organisms, or from an unrelated recombinant protein control expressed and purified in the same way, were subjected to SDS-PAGE containing 12% acrylamide. A cell lysate of pneumococcal strain SJ2 (serotype 6B) was also included on the gel. After electrophoresis, the separated proteins were transferred to a nitrocellulose membrane and probed with rabbit polyclonal antiserum raised against the recombinant pneumococcal protein. Bound antibodies were detected chemiluminescently with a goat anti-rabbit IgG antibody conjugated to horseradish peroxidase using the substrate ECL (from Amersham). The results demonstrate that antiserum raised against the pneumococcal Sp36 protein cross-react with the Sp36 homolog identified from the group B streptococci and thereby indicating conservation of epitopes between the proteins. The group B streptococcal homolog is also approximately the same size as the protein detected in *S. pneumoniae* lysates. Because the group A and B homologs are highly homologous, if not identical, such antiserum would also likely cross-react with the group A streptococcal protein.

EXAMPLE 5

Alignment of Predicted Amino Acid Sequences of the Sp36 Homologs from group A and B Streptococci with Pneumococcal Sp36

The predicted amino acid sequences from the Sp36 genes from group A and group B streptococci and *S. pneumoniae* were aligned using the Clustal algorithm in a DNAStar Computer package (DNAStar, Inc., Madison, Wis.). Amino acids that match those encoded by the pneumococcal gene are boxed in FIG. 2 (showing the results of the alignment). Gaps introduced in the sequence by the alignment process are indicated by dashed lines.

EXAMPLE 6

Percentage Sequence Identity Between Homologs of Sp36

The Sp36 amino acid sequence from pneumococci is 25.6% identical to the predicted amino acid sequence of the homologous gene of group B streptococci and 25.1% and 12.6% identical to the deduced sequences of the two genes from group A streptococci. Furthermore, the group B homolog is 97.7% and 11.6% identical to the first (GAS36) and second (GAS36(2)) homologs from group A streptococci, respectively. These experiments indicate that homologous genes to Sp36 from pneumococcus are present in group A and group B streptococci, as well as in *Staphylococcus aureus*. The protein encoded by this gene may therefore perform a similar function in these different organisms. This suggests that a vaccine comprising one or more of these proteins may be broadly protective against these species. These results are summarized in Table 1 which shows the percent identity between the amino acid sequences of Sp36 from pneumococcus strain Norway 4 (serotype 4), group A streptococci Sp36 homolog from an M1 serotype, and group B streptococci Sp36 from strain R268.

TABLE 1

|  | Pneumo. Sp36 | GAS36 | GAS36(2) | GBS36 |
| --- | --- | --- | --- | --- |
| Pneumo. Sp36 | 100% | 25.1% | 12.6% | 25.6% |
| GAS36 | — | 100% |  | 97.7% |
| GAS36(2) | — | — | 100% | 11.6% |
| GBS36 | — | — |  | 100% | where
GAS36 = SEQ ID NO: 2
GAS36(2) = SEQ ID NO: 4
GBS36 = SEQ ID NO: 6

What is claimed is:

1. An isolated polypeptide comprising an amino acid sequence with at least 95% sequence identity to the sequence of SEQ ID NO: 4 and wherein said polypeptide binds to an antibody that is specific for Sp36 (SEQ ID NO: 7).

2. An isolated polypeptide comprising an amino acid sequence with at least 95% sequence identity to a sequence selected from the group consisting of SEQ ID NO: 2 and 4 wherein said polypeptide is identical to that found in an organism selected from the group consisting of Group A streptococci and *Staphylococcus aureus* and wherein said polypeptide binds to an antibody that is specific for Sp36 (SEQ ID NO: 7).

3. The isolated polypeptide of claim 2 wherein said Group A organism is *Streptococcus pyogenes*.

4. The isolated polypeptide of claim 2 wherein said organism is *Staphylococcus aureus*.

5. An isolated polypepbde comprising an amino acid sequence at least 95% identical to the sequence of SEQ ID NO: 4 and wherein said polypeptide has a sequence with at least 12.6% sequence identity to the amino acid sequence of the Sp36 protein (SEQ ID NO: 7) of *Streptococcus pneumoniae* and wherein said isolated polypeptide binds to an antibody that is specific for Sp36.

6. An isolated polypeptide comprising the sequence of SEQ ID NO: 2 wherein said isolated polypeptide binds to an antibody that is specific for Sp36 (SEQ ID NO: 7) of *Streptococcus pneumoniae*.

7. An isolated polypeptide comprising the amino acid sequence of SEQ ID NO: 2.

8. An isolated polypeptide comprising the amino acid sequence of SEQ ID NO: 4.

* * * * *

SEQUENCE LISTING

<160> NUMBER OF SEQ ID NOS: 7

<210> SEQ ID NO 1
<211> LENGTH: 2478
<212> TYPE: DNA
<213> ORGANISM: Streptococcus pyogenes

<400> SEQUENCE: 1

```
gtgaagaaaa catatggtta tatcggctca gttgctgcta ttttactagc tactcatatt      60
ggaagttacc aacttggtaa gcatcatatg ggttcagcaa caaaggacaa tcaaattgcc     120
tatattgatg atagcaaagg taaggcaaaa gcccctaaaa caaacaaaac gatggatcaa     180
atcagtgctg aagaaggcat ctctgctgaa cagatcgtag tcaaaattac tgaccaaggc     240
tatgtgacct cacatggtga ccattatcat ttttacaatg ggaaagttcc ttatgatgcg     300
attattagtg aagagttgtt gatgacggat cctaattacc gttttaaaca atcagacgtt     360
atcaatgaaa tcttagacgg ttacgttatt aaagtcaatg gcaactatta tgtttacctc     420
aagccaggta gcaagcgcaa aaacattcga accaaacaac aaattgctga gcaagtagcc     480
aaaggaacta aagaagctaa agaaaaaggt ttagctcaag tggcccatct cagtaaagaa     540
```

| | | | | |
|---|---|---|---|---|
| gaagttgcgg | cagtcaatga | agcaaaaaga | caaggacgct | atactacaga cgatggctat | 600 |
| atttttagtc | cgacagatat | cattgatgat | ttaggagatg | cttatttagt acctcatggt | 660 |
| aatcactatc | attatattcc | taaaaaggat | ttgtctccaa | gtgagctagc tgctgcacaa | 720 |
| gcctactgga | gtcaaaaaca | aggtcgaggt | gctagaccgt | ctgattaccg cccgacacca | 780 |
| gccccagccc | caggtcgtag | gaaagcccca | attcctgatg | tgacgcctaa ccctggacaa | 840 |
| ggtcatcagc | cagataacgg | tggctatcat | ccagcgcctc | ctaggccaaa tgatgcgtca | 900 |
| caaaacaaac | accaaagaga | tgagtttaaa | ggaaaaacct | taaggaact tttagatcaa | 960 |
| ctacaccgtc | ttgatttgaa | ataccgtcat | gtggaagaag | atgggttgat ttttgaaccg | 1020 |
| actcaagtga | tcaaatcaaa | cgcttttggg | tatgtggtgc | ctcatggaga tcattatcat | 1080 |
| attatcccaa | gaagtcagtt | atcacctctt | gaatggaat | tagcagatcg atacttagcc | 1140 |
| ggccaaactg | aggacgatga | ctcaggttca | gatcactcaa | aaccatcaga taagaagtg | 1200 |
| acacatacct | tcttggtca | tcgcatcaaa | gcttacggaa | aaggcttaga tggtaaacca | 1260 |
| tatgatacga | gtgatgctta | tgttttagt | aaagaatcca | ttcattcagt ggataaatca | 1320 |
| ggagttacag | ctaaacacgg | agatcatttc | cactatatag | gatttggaga acttgaacaa | 1380 |
| tatgagttgg | atgaggtcgc | taactgggtg | aaagcaaaag | gtcaagctga tgagcttgct | 1440 |
| gctgctttgg | atcaggaaca | aggcaaagaa | aaaccactct | ttgacactaa aaaagtgagt | 1500 |
| cgcaaagtaa | caaagatgg | taaagtgggc | tatatgatgc | caaagatgg caaggactat | 1560 |
| ttctatgctc | gtgatcaact | tgatttgact | cagattgcct | ttgccgaaca agaactaatg | 1620 |
| cttaaagata | gaaacatta | ccgttatgac | attgttgaca | caggtattga gccacgactt | 1680 |
| gctgtagatg | tgtcaagtct | gccgatgcat | gctggtaatg | ctacttacga tactggaagt | 1740 |
| tcgtttgtta | tccctcatat | tgatcatatc | catgtcgttc | cgtattcatg gttgacgcgc | 1800 |
| gatcagattg | caacaatcaa | gtatgtgatg | caacaccccg | aagttcgtcc ggatatatgg | 1860 |
| tctaagccag | ggcatgaaga | gtcaggttcg | gtcattccaa | atgttacgcc tcttgataaa | 1920 |
| cgtgctggta | tgccaaactg | gcaaattatc | cattctgctg | aagaagttca aaaagcccta | 1980 |
| gcagaaggtc | gttttgcaac | accagacggc | tatattttcg | atccacgaga tgttttggcc | 2040 |
| aaagaaactt | ttgtatggaa | agatggctcc | tttagcatcc | aagagcaga tggcagttca | 2100 |
| ttgagaacca | ttaataaatc | tgatctatcc | caagctgagt | ggcaacaagc tcaagagtta | 2160 |
| ttggcaaaga | aaaacgctgg | tgatgctact | gatacggata | aacccaaaga aaagcaacag | 2220 |
| gcagataaga | gcaatgaaaa | ccaacagcca | agtgaagcca | gtaaagaaga agaaaaagaa | 2280 |
| tcagatgact | ttatagacag | tttaccagac | tatggtctag | atagagcaac cctagaagat | 2340 |
| catatcaatc | aattagcaca | aaaagctaat | atcgatccta | agtatctcat tttccaacca | 2400 |
| gaaggtgtcc | aattttataa | taaaaatggt | gaattggtaa | cttatgatat caagacactt | 2460 |
| caacaaataa | acccttaa | | | | 2478 |

<210> SEQ ID NO 2
<211> LENGTH: 825
<212> TYPE: PRT
<213> ORGANISM: Streptococcus pyogenes

<400> SEQUENCE: 2

Val Lys Lys Thr Tyr Gly Tyr Ile Gly Ser Val Ala Ala Ile Leu Leu
 1               5                  10                  15

Ala Thr His Ile Gly Ser Tyr Gln Leu Gly Lys His His Met Gly Ser

-continued

```
              20                  25                  30
Ala Thr Lys Asp Asn Gln Ile Ala Tyr Ile Asp Asp Ser Lys Gly Lys
            35                  40                  45

Ala Lys Ala Pro Lys Thr Asn Lys Thr Met Asp Gln Ile Ser Ala Glu
 50                  55                  60

Glu Gly Ile Ser Ala Glu Gln Ile Val Val Lys Ile Thr Asp Gln Gly
 65                  70                  75                  80

Tyr Val Thr Ser His Gly Asp His Tyr His Phe Tyr Asn Gly Lys Val
                85                  90                  95

Pro Tyr Asp Ala Ile Ile Ser Glu Glu Leu Leu Met Thr Asp Pro Asn
                100                 105                 110

Tyr Arg Phe Lys Gln Ser Asp Val Ile Asn Glu Ile Leu Asp Gly Tyr
            115                 120                 125

Val Ile Lys Val Asn Gly Asn Tyr Tyr Val Tyr Leu Lys Pro Gly Ser
            130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
            180                 185                 190

Arg Tyr Thr Thr Asp Asp Gly Tyr Ile Phe Ser Pro Thr Asp Ile Ile
            195                 200                 205

Asp Asp Leu Gly Asp Ala Tyr Leu Val Pro His Gly Asn His Tyr His
210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
                245                 250                 255

Arg Pro Thr Pro Ala Pro Ala Pro Gly Arg Arg Lys Ala Pro Ile Pro
            260                 265                 270

Asp Val Thr Pro Asn Pro Gly Gln Gly His Gln Pro Asp Asn Gly Gly
            275                 280                 285

Tyr His Pro Ala Pro Arg Pro Asn Asp Ala Ser Gln Asn Lys His
            290                 295                 300

Gln Arg Asp Glu Phe Lys Gly Lys Thr Phe Lys Glu Leu Leu Asp Gln
305                 310                 315                 320

Leu His Arg Leu Asp Leu Lys Tyr Arg His Val Glu Glu Asp Gly Leu
                325                 330                 335

Ile Phe Glu Pro Thr Gln Val Ile Lys Ser Asn Ala Phe Gly Tyr Val
            340                 345                 350

Val Pro His Gly Asp His Tyr His Ile Ile Pro Arg Ser Gln Leu Ser
            355                 360                 365

Pro Leu Glu Met Glu Leu Ala Asp Arg Tyr Leu Ala Gly Gln Thr Glu
            370                 375                 380

Asp Asp Asp Ser Gly Ser Asp His Ser Lys Pro Ser Asp Lys Glu Val
385                 390                 395                 400

Thr His Thr Phe Leu Gly His Arg Ile Lys Ala Tyr Gly Lys Gly Leu
                405                 410                 415

Asp Gly Lys Pro Tyr Asp Thr Ser Asp Ala Tyr Val Phe Ser Lys Glu
            420                 425                 430

Ser Ile His Ser Val Asp Lys Ser Gly Val Thr Ala Lys His Gly Asp
            435                 440                 445
```

His Phe His Tyr Ile Gly Phe Gly Glu Leu Glu Gln Tyr Glu Leu Asp
    450                 455                 460
Glu Val Ala Asn Trp Val Lys Ala Lys Gly Gln Ala Asp Glu Leu Ala
465                 470                 475                 480
Ala Ala Leu Asp Gln Glu Gln Gly Lys Glu Lys Pro Leu Phe Asp Thr
                485                 490                 495
Lys Lys Val Ser Arg Lys Val Thr Lys Asp Gly Lys Val Gly Tyr Met
            500                 505                 510
Met Pro Lys Asp Gly Lys Asp Tyr Phe Tyr Ala Arg Asp Gln Leu Asp
        515                 520                 525
Leu Thr Gln Ile Ala Phe Ala Glu Gln Glu Leu Met Leu Lys Asp Lys
    530                 535                 540
Lys His Tyr Arg Tyr Asp Ile Val Asp Thr Gly Ile Glu Pro Arg Leu
545                 550                 555                 560
Ala Val Asp Val Ser Ser Leu Pro Met His Ala Gly Asn Ala Thr Tyr
                565                 570                 575
Asp Thr Gly Ser Ser Phe Val Ile Pro His Ile Asp His Ile His Val
            580                 585                 590
Val Pro Tyr Ser Trp Leu Thr Arg Asp Gln Ile Ala Thr Ile Lys Tyr
        595                 600                 605
Val Met Gln His Pro Glu Val Arg Pro Asp Ile Trp Ser Lys Pro Gly
    610                 615                 620
His Glu Glu Ser Gly Ser Val Ile Pro Asn Val Thr Pro Leu Asp Lys
625                 630                 635                 640
Arg Ala Gly Met Pro Asn Trp Gln Ile Ile His Ser Ala Glu Glu Val
                645                 650                 655
Gln Lys Ala Leu Ala Glu Gly Arg Phe Ala Thr Pro Asp Gly Tyr Ile
            660                 665                 670
Phe Asp Pro Arg Asp Val Leu Ala Lys Glu Thr Phe Val Trp Lys Asp
        675                 680                 685
Gly Ser Phe Ser Ile Pro Arg Ala Asp Gly Ser Ser Leu Arg Thr Ile
    690                 695                 700
Asn Lys Ser Asp Leu Ser Gln Ala Glu Trp Gln Gln Ala Gln Glu Leu
705                 710                 715                 720
Leu Ala Lys Lys Asn Ala Gly Asp Ala Thr Asp Thr Asp Lys Pro Lys
                725                 730                 735
Glu Lys Gln Gln Ala Asp Lys Ser Asn Glu Asn Gln Gln Pro Ser Glu
            740                 745                 750
Ala Ser Lys Glu Glu Glu Lys Glu Ser Asp Asp Phe Ile Asp Ser Leu
        755                 760                 765
Pro Asp Tyr Gly Leu Asp Arg Ala Thr Leu Glu Asp His Ile Asn Gln
    770                 775                 780
Leu Ala Gln Lys Ala Asn Ile Asp Pro Lys Tyr Leu Ile Phe Gln Pro
785                 790                 795                 800
Glu Gly Val Gln Phe Tyr Asn Lys Asn Gly Glu Leu Val Thr Tyr Asp
                805                 810                 815
Ile Lys Thr Leu Gln Gln Ile Asn Pro
            820                 825

<210> SEQ ID NO 3
<211> LENGTH: 2379
<212> TYPE: DNA
<213> ORGANISM: Streptococcus pyogenes -continued

```
<400> SEQUENCE: 3
atgaaaacga aaaaagttat tattttagtt ggtctattgt tatcatctca gttgactttg      60
atagcttgtc aatcacgagg taatggtaca tatcccatta aaacgaaaca atcacgtaag     120
ggaatgacgt caaacaaaat taaaccgatt aaaaaaagca aaaagacaaa caagactcac     180
aaaggtgtgg cggtgtcga ttttcctaca gatgatgggt ttattttaac caaagactca     240
aaaatcttat caaaaacaga tcagggaatc gttgttgacc atgatggtca ttcgcatttt     300 atttttatg ccgatttaaa gggaagtcca tttgaatacc ttattccaaa aggagcaagt     360
ttagctaagc cagctgttgc tcagcgagca gctagtcaag ggacttctaa agtagcagat     420
cctcatcacc attatgaatt taacccagcg gatattgtgg ctgaagatgc tttaggctac     480
acggttcgcc acgatgatca cttccattat attttgaagt caagcttatc aggtcagaca     540
caggcacaag ctaaacaggt tgctactcgc ttgccacaaa ccagtagcct tgtttcaaca     600
gctacagcta atggtattcc aggcttgcat ttcccaacct cagatggttt tcaatttaac     660
ggtcaaggta ttgttggggt aacaaaagac agtattttag tggaccacga tggtcactta     720
catcctattt cttttgcgga ccttcgtcag ggtggctggg cacatgtggc agatcaatac     780
gatcccgcta aaaagcaga aaagccagca gaaacccatc agacaccaga gctatctgaa     840
cgtgaaaagg aataccaaga aaaattagct tatttggcag aaaaattggg gattgatcca     900
tcaactatta aacgtgtgga acacaagac ggtaaacttg gtttggaata ccctcaccat     960
gaccacgcac acgtattgat gttatctgat attgaaatcg aaaagacat tccagatcca    1020 catgctattg agcatgcccg tgaattggaa aaacataagg ttggaatgga taccttgcgt    1080
gccttagggt ttgatgaaga agtgattttg gatatcgttc gcactcacga tgctccaacc    1140
ccattcccat caaatgaaaa agatccgaat atgatgaaag aatggttagc aacggttatc    1200
aaacttgact gggcagccg taaagatcct ttgcaacgta aaggacttc actgttaccc    1260 aacttagaaa ctttaggaat tggctttaca ccaatcaaag atatctcacc tgttttgcaa    1320
tttaaaaaat tgaaacagtt gttaatgaca aaaacagggg tgactgatta tagattttg    1380 gataatatgc cacagttaga aggcattgat atttcacaaa acaatctcaa agatattagt    1440
ttcttgagca aatataaaaa cttaactcta gtagcggctg ctgataatgg tattgaagat    1500
attaggccgc ttggtcaatt accaaatctc aaattcctcg tattgagtaa caataagatt    1560
tctgatttaa gcccactggc atcgttacat caattgcaag aattgcacat tgataataat    1620
cagattacag atttaagccc tgtttctcat aaagaatcat tgacggttgt tgatttatca    1680
agaaatgctg atgttgactt agcaacactt caagcaccca attagaaaac gttaatggtc    1740
aatgatacca aggtttctca tttggatttc ttgaaaaata tcctaatct atctagccta    1800 tctattaacc gtgcgcaatt gcaatctctt gaaggtattg aagcaagtag cgtcattgtc    1860
agagtagaag cagaaggtaa ccaaattaaa tcgcttgtgc ttaaagacaa gcaagggtca    1920
cttactttct tggatgtgac aggcaaccag ttgacttctc tagaaggtgt taataatttt    1980
acagcacttg acatttaag cgtgtctaaa aaccaattaa caaatgtcaa cctatctaaa    2040
cccaataaga cagttactaa cattgatatt agtcataaca atatctcatt agcagacctt    2100
aaattgaacg agcaacatat tccagaagcc attgcgaaaa acttcccagc ggtttacgaa    2160
ggttctatgg taggtaatgg aacagctgaa gaaaaagcag ctatggctac taaggcgaaa    2220
gaaagtgctc aagaagcatc ggaatcacat gactacaacc ataatcatac ctatgaagat    2280
gaagaaggtc atgctcacga gcacagagac aaagatgatc acgaccatga acatgaggat    2340
```

-continued gaaaatgaag ctaaagatga gcaaaaccat gctgactaa                             2379

<210> SEQ ID NO 4
<211> LENGTH: 792
<212> TYPE: PRT
<213> ORGANISM: Streptococcus pyogenes

<400> SEQUENCE: 4

Met Lys Thr Lys Lys Val Ile Ile Leu Val Gly Leu Leu Ser Ser
 1               5                  10                  15

Gln Leu Thr Leu Ile Ala Cys Gln Ser Arg Gly Asn Gly Thr Tyr Pro
            20                  25                  30

Ile Lys Thr Lys Gln Ser Arg Lys Gly Met Thr Ser Asn Lys Ile Lys
        35                  40                  45

Pro Ile Lys Lys Ser Lys Lys Thr Asn Lys Thr His Lys Gly Val Ala
    50                  55                  60

Gly Val Asp Phe Pro Thr Asp Asp Gly Phe Ile Leu Thr Lys Asp Ser
65                  70                  75                  80

Lys Ile Leu Ser Lys Thr Asp Gln Gly Ile Val Val Asp His Asp Gly
                85                  90                  95

His Ser His Phe Ile Phe Tyr Ala Asp Leu Lys Gly Ser Pro Phe Glu
            100                 105                 110

Tyr Leu Ile Pro Lys Gly Ala Ser Leu Ala Lys Pro Ala Val Ala Gln
        115                 120                 125

Arg Ala Ala Ser Gln Gly Thr Ser Lys Val Ala Asp Pro His His His
    130                 135                 140

Tyr Glu Phe Asn Pro Ala Asp Ile Val Ala Glu Asp Ala Leu Gly Tyr
145                 150                 155                 160

Thr Val Arg His Asp Asp His Phe His Tyr Ile Leu Lys Ser Ser Leu
                165                 170                 175

Ser Gly Gln Thr Gln Ala Gln Ala Lys Gln Val Ala Thr Arg Leu Pro
            180                 185                 190

Gln Thr Ser Ser Leu Val Ser Thr Ala Thr Ala Asn Gly Ile Pro Gly
        195                 200                 205

Leu His Phe Pro Thr Ser Asp Gly Phe Gln Phe Asn Gly Gln Gly Ile
    210                 215                 220

Val Gly Val Thr Lys Asp Ser Ile Leu Val Asp His Asp Gly His Leu
225                 230                 235                 240

His Pro Ile Ser Phe Ala Asp Leu Arg Gln Gly Gly Trp Ala His Val
                245                 250                 255

Ala Asp Gln Tyr Asp Pro Ala Lys Lys Ala Glu Lys Pro Ala Glu Thr
            260                 265                 270

His Gln Thr Pro Glu Leu Ser Glu Arg Glu Lys Glu Tyr Gln Glu Lys
        275                 280                 285

Leu Ala Tyr Leu Ala Glu Lys Leu Gly Ile Asp Pro Ser Thr Ile Lys
    290                 295                 300

Arg Val Glu Thr Gln Asp Gly Lys Leu Gly Leu Glu Tyr Pro His His
305                 310                 315                 320

Asp His Ala His Val Leu Met Leu Ser Asp Ile Glu Ile Gly Lys Asp
                325                 330                 335

Ile Pro Asp Pro His Ala Ile Glu His Ala Arg Glu Leu Glu Lys His
            340                 345                 350

Lys Val Gly Met Asp Thr Leu Arg Ala Leu Gly Phe Asp Glu Glu Val
        355                 360                 365

```
Ile Leu Asp Ile Val Arg Thr His Asp Ala Pro Thr Pro Phe Pro Ser
    370                 375                 380

Asn Glu Lys Asp Pro Asn Met Met Lys Glu Trp Leu Ala Thr Val Ile
385                 390                 395                 400

Lys Leu Asp Leu Gly Ser Arg Lys Asp Pro Leu Gln Arg Lys Gly Leu
                405                 410                 415

Ser Leu Leu Pro Asn Leu Glu Thr Leu Gly Ile Gly Phe Thr Pro Ile
            420                 425                 430

Lys Asp Ile Ser Pro Val Leu Gln Phe Lys Lys Leu Lys Gln Leu Leu
        435                 440                 445

Met Thr Lys Thr Gly Val Thr Asp Tyr Arg Phe Leu Asp Asn Met Pro
    450                 455                 460

Gln Leu Glu Gly Ile Asp Ile Ser Gln Asn Asn Leu Lys Asp Ile Ser
465                 470                 475                 480

Phe Leu Ser Lys Tyr Lys Asn Leu Thr Leu Val Ala Ala Ala Asp Asn
                485                 490                 495

Gly Ile Glu Asp Ile Arg Pro Leu Gly Gln Leu Pro Asn Leu Lys Phe
            500                 505                 510

Leu Val Leu Ser Asn Asn Lys Ile Ser Asp Leu Ser Pro Leu Ala Ser
        515                 520                 525

Leu His Gln Leu Gln Glu Leu His Ile Asp Asn Asn Gln Ile Thr Asp
    530                 535                 540

Leu Ser Pro Val Ser His Lys Glu Ser Leu Thr Val Val Asp Leu Ser
545                 550                 555                 560

Arg Asn Ala Asp Val Asp Leu Ala Thr Leu Gln Ala Pro Lys Leu Glu
                565                 570                 575

Thr Leu Met Val Asn Asp Thr Lys Val Ser His Leu Asp Phe Leu Lys
            580                 585                 590

Asn Asn Pro Asn Leu Ser Ser Leu Ser Ile Asn Arg Ala Gln Leu Gln
        595                 600                 605

Ser Leu Glu Gly Ile Glu Ala Ser Ser Val Ile Val Arg Val Glu Ala
    610                 615                 620

Glu Gly Asn Gln Ile Lys Ser Leu Val Leu Lys Asp Lys Gln Gly Ser
625                 630                 635                 640

Leu Thr Phe Leu Asp Val Thr Gly Asn Gln Leu Thr Ser Leu Glu Gly
                645                 650                 655

Val Asn Asn Phe Thr Ala Leu Asp Ile Leu Ser Val Ser Lys Asn Gln
            660                 665                 670

Leu Thr Asn Val Asn Leu Ser Lys Pro Asn Lys Thr Val Thr Asn Ile
        675                 680                 685

Asp Ile Ser His Asn Asn Ile Ser Leu Ala Asp Leu Lys Leu Asn Glu
    690                 695                 700

Gln His Ile Pro Glu Ala Ile Ala Lys Asn Phe Pro Ala Val Tyr Glu
705                 710                 715                 720

Gly Ser Met Val Gly Asn Gly Thr Ala Glu Glu Lys Ala Ala Met Ala
                725                 730                 735

Thr Lys Ala Lys Glu Ser Ala Gln Glu Ala Ser Glu Ser His Asp Tyr
            740                 745                 750

Asn His Asn His Thr Tyr Glu Asp Glu Gly His Ala His Glu His
        755                 760                 765

Arg Asp Lys Asp Asp His Asp His Glu His Glu Asp Glu Asn Glu Ala
770                 775                 780
```

Lys Asp Glu Gln Asn His Ala Asp
785             790

<210> SEQ ID NO 5
<211> LENGTH: 2469
<212> TYPE: DNA
<213> ORGANISM: Streptococcus agalactiae

<400> SEQUENCE: 5

| | | | | | |
|---|---|---|---|---|---|
| gtgaagaaaa | catatggtta | tatcggctca | gttgctgcta | ttttactagc | tactcatatt | 60 |
| ggaagttacc | agcttggtaa | gcatcatatg | ggtctagcaa | caaaggacaa | tcagattgcc | 120 |
| tatattgatg | atagcaaagg | taaggtaaaa | gcccctaaaa | caaacaaaac | gatggatcaa | 180 |
| atcagtgctg | aagaaggcat | ctctgctgaa | cagatcgtag | tcaaaattac | tgaccaaggt | 240 |
| tatgttacct | cacacggtga | ccattatcat | ttttacaatg | ggaaagttcc | ttatgatgcg | 300 |
| attattagtg | aagagttgtt | gatgacggat | cctaattacc | attttaaaca | atcagacgtt | 360 |
| atcaatgaaa | tcttagacgg | ttacgttatt | aaagtcaatg | gcaactatta | tgtttacctc | 420 |
| aagccaggta | gtaagcgcaa | aaacattcga | accaaacaac | aaattgctga | gcaagtagcc | 480 |
| aaaggaacta | agaagctaa | agaaaaaggt | ttagctcaag | tggcccatct | cagtaaagaa | 540 |
| gaagttgcgg | cagtcaatga | agcaaaaaga | caaggacgct | atactacaga | cgatggctat | 600 |
| attttagtc | cgacagatat | cattgatgat | ttaggagatg | cttatttagt | acctcatggt | 660 |
| aatcactatc | attatattcc | taaaaaagat | ttgtctccaa | gtgagctagc | tgctgcacaa | 720 |
| gcctactgga | gtcaaaaaca | aggtcgaggt | gctagaccgt | ctgattaccg | cccgacacca | 780 |
| gccccaggtc | gtaggaaagc | cccaattcct | gatgtgacgc | taaccctgg | acaaggtcat | 840 |
| cagccagata | acggtggtta | tcatccagcg | cctcctaggc | caaatgatgc | gtcacaaaac | 900 |
| aaacaccaaa | gagatgagtt | taaggaaaa | accttttaagg | aactttttaga | tcaactacac | 960 |
| cgtcttgatt | tgaaataccg | tcatgtggaa | gaagatgggg | tgattttttga | accgactcaa | 1020 |
| gtgatcaaat | caaacgcttt | tgggtatgtg | gtgcctcatg | gagatcatta | tcatattatc | 1080 |
| ccaagaagtc | agttataccc | acttgaaatg | gaattagcag | atcgatactt | agccggccaa | 1140 |
| actgatgaca | acgactcagg | ttcagatcac | tcaaaaccat | cagataaaga | agtgacacat | 1200 |
| acctttcttg | gtcatcgcat | caaagcttac | ggaaaaggct | tagatggtaa | accatatgat | 1260 |
| acgagtgatg | cttatgtttt | tagtaaagaa | tccattcatt | cagtggataa | atcaggagtt | 1320 |
| acagctaaac | acggagatca | tttccactat | ataggatttg | gagaacttga | acaatatgag | 1380 |
| ttggatgagg | tcgctaactg | ggtgaaagca | aaaggtcaag | ctgatgagct | tgttgctgct | 1440 |
| ttggatcagg | aacaaggcaa | agaaaaacca | ctctttgaca | ctaaaaaagt | gagtcgcaaa | 1500 |
| gtaacaaaag | atggtaaagt | gggctatatt | atgccaaaag | atggcaagga | ctatttctat | 1560 |
| gctcgttatc | aacttgattt | gactcagatt | gcctttgccg | aacaagaact | aatgcttaaa | 1620 |
| gataagaagc | attaccgtta | tgacattgtt | gatacaggca | ttgagccacg | acttgctgta | 1680 |
| gatgtgtcaa | gtctgccgat | gcatgctggt | aatgctactt | acgatactgg | aagttcgttt | 1740 |
| gttatcccac | atattgatca | tatccatgtc | gttccgtatt | catggttgac | gcgcaatcag | 1800 |
| attgcaacaa | tcaagtatgt | gatgcaacac | cccgaagttc | gtccggatgt | atggtctaag | 1860 |
| ccagggcatg | aagagtcagg | ttcggtcatt | ccaaatgtta | cgcctcttga | taacgtgct | 1920 |
| ggtatgccaa | actggcaaat | tatccattct | gctgaagaag | ttcaaaaagc | cctagcagaa | 1980 |
| ggtcgttttg | cagcaccaga | cggctatatt | ttcgatccac | gagatgtttt | ggcaaaagaa | 2040 |

-continued

```
acttttgtat ggaaagatgg ctcctttagc atcccaagag cagatggcag ttcattgaga    2100
accattaata aatccgatct atcccaagct gagtggcaac aagctcaaga gttattggca    2160
aagaaaaatg ctggtgatgc tactgatacg gataaacctg aagaaaagca acaggcagat    2220
aagagcaatg aaaaccaaca gccaagtgaa gccagtaaaa agaaaaaaga atcagatgac    2280
tttatagaca gtttaccaga ctatggtcta gatagagcaa ccctagaaga tcatatcaat    2340
caattagcac aaaaagctaa tatcgatcct aagtatctca ttttccaacc agaaggtgtc    2400 caatttttata ataaaaatgg tgaattggta acttatgata tcaagacact tcaacaaata    2460
aacccttaa                                                            2469
```

<210> SEQ ID NO 6
<211> LENGTH: 822
<212> TYPE: PRT
<213> ORGANISM: Streptococcus agalactiae

<400> SEQUENCE: 6

```
Val Lys Lys Thr Tyr Gly Tyr Ile Gly Ser Val Ala Ala Ile Leu Leu
  1               5                  10                  15

Ala Thr His Ile Gly Ser Tyr Gln Leu Gly Lys His His Met Gly Leu
             20                  25                  30

Ala Thr Lys Asp Asn Gln Ile Ala Tyr Ile Asp Asp Ser Lys Gly Lys
         35                  40                  45

Val Lys Ala Pro Lys Thr Asn Lys Thr Met Asp Gln Ile Ser Ala Glu
     50                  55                  60

Glu Gly Ile Ser Ala Glu Gln Ile Val Val Lys Ile Thr Asp Gln Gly
 65                  70                  75                  80

Tyr Val Thr Ser His Gly Asp His Tyr His Phe Tyr Asn Gly Lys Val
                 85                  90                  95

Pro Tyr Asp Ala Ile Ile Ser Glu Glu Leu Leu Met Thr Asp Pro Asn
            100                 105                 110

Tyr His Phe Lys Gln Ser Asp Val Ile Asn Glu Ile Leu Asp Gly Tyr
        115                 120                 125

Val Ile Lys Val Asn Gly Asn Tyr Tyr Val Tyr Leu Lys Pro Gly Ser
    130                 135                 140

Lys Arg Lys Asn Ile Arg Thr Lys Gln Gln Ile Ala Glu Gln Val Ala
145                 150                 155                 160

Lys Gly Thr Lys Glu Ala Lys Glu Lys Gly Leu Ala Gln Val Ala His
                165                 170                 175

Leu Ser Lys Glu Glu Val Ala Ala Val Asn Glu Ala Lys Arg Gln Gly
            180                 185                 190

Arg Tyr Thr Thr Asp Asp Gly Tyr Ile Phe Ser Pro Thr Asp Ile Ile
        195                 200                 205

Asp Asp Leu Gly Asp Ala Tyr Leu Val Pro His Gly Asn His Tyr His
    210                 215                 220

Tyr Ile Pro Lys Lys Asp Leu Ser Pro Ser Glu Leu Ala Ala Ala Gln
225                 230                 235                 240

Ala Tyr Trp Ser Gln Lys Gln Gly Arg Gly Ala Arg Pro Ser Asp Tyr
                245                 250                 255

Arg Pro Thr Pro Ala Pro Gly Arg Arg Lys Ala Pro Ile Pro Asp Val
            260                 265                 270

Thr Pro Asn Pro Gly Gln Gly His Gln Pro Asp Asn Gly Gly Tyr His
        275                 280                 285

Pro Ala Pro Pro Arg Pro Asn Asp Ala Ser Gln Asn Lys His Gln Arg
```

-continued

```
              290                 295                 300
Asp Glu Phe Lys Gly Lys Thr Phe Lys Glu Leu Leu Asp Gln Leu His
305                 310                 315                 320

Arg Leu Asp Leu Lys Tyr Arg His Val Glu Glu Asp Gly Leu Ile Phe
                325                 330                 335

Glu Pro Thr Gln Val Ile Lys Ser Asn Ala Phe Gly Tyr Val Val Pro
                340                 345                 350

His Gly Asp His Tyr His Ile Ile Pro Arg Ser Gln Leu Ser Pro Leu
                355                 360                 365

Glu Met Glu Leu Ala Asp Arg Tyr Leu Ala Gly Gln Thr Asp Asp Asn
370                 375                 380

Asp Ser Gly Ser Asp His Ser Lys Pro Ser Asp Lys Glu Val Thr His
385                 390                 395                 400

Thr Phe Leu Gly His Arg Ile Lys Ala Tyr Gly Lys Gly Leu Asp Gly
                405                 410                 415

Lys Pro Tyr Asp Thr Ser Asp Ala Tyr Val Phe Ser Lys Glu Ser Ile
                420                 425                 430

His Ser Val Asp Lys Ser Gly Val Thr Ala Lys His Gly Asp His Phe
                435                 440                 445

His Tyr Ile Gly Phe Gly Glu Leu Glu Gln Tyr Glu Leu Asp Glu Val
                450                 455                 460

Ala Asn Trp Val Lys Ala Lys Gly Gln Ala Asp Glu Leu Val Ala Ala
465                 470                 475                 480

Leu Asp Gln Glu Gln Gly Lys Glu Lys Pro Leu Phe Asp Thr Lys Lys
                485                 490                 495

Val Ser Arg Lys Val Thr Lys Asp Gly Lys Val Gly Tyr Ile Met Pro
                500                 505                 510

Lys Asp Gly Lys Asp Tyr Phe Tyr Ala Arg Tyr Gln Leu Asp Leu Thr
                515                 520                 525

Gln Ile Ala Phe Ala Glu Gln Leu Met Leu Lys Asp Lys Lys His
                530                 535                 540

Tyr Arg Tyr Asp Ile Val Asp Thr Gly Ile Glu Pro Arg Leu Ala Val
545                 550                 555                 560

Asp Val Ser Ser Leu Pro Met His Ala Gly Asn Ala Thr Tyr Asp Thr
                565                 570                 575

Gly Ser Ser Phe Val Ile Pro His Ile Asp His Ile His Val Val Pro
                580                 585                 590

Tyr Ser Trp Leu Thr Arg Asn Gln Ile Ala Thr Ile Lys Tyr Val Met
                595                 600                 605

Gln His Pro Glu Val Arg Pro Asp Val Trp Ser Lys Pro Gly His Glu
                610                 615                 620

Glu Ser Gly Ser Val Ile Pro Asn Val Thr Pro Leu Asp Lys Arg Ala
625                 630                 635                 640

Gly Met Pro Asn Trp Gln Ile Ile His Ser Ala Glu Val Gln Lys
                645                 650                 655

Ala Leu Ala Glu Gly Arg Phe Ala Ala Pro Asp Gly Tyr Ile Phe Asp
                660                 665                 670

Pro Arg Asp Val Leu Ala Lys Glu Thr Phe Val Trp Lys Asp Gly Ser
                675                 680                 685

Phe Ser Ile Pro Arg Ala Asp Gly Ser Ser Leu Arg Thr Ile Asn Lys
                690                 695                 700

Ser Asp Leu Ser Gln Ala Glu Trp Gln Gln Ala Gln Glu Leu Leu Ala
705                 710                 715                 720
```

```
Lys Lys Asn Ala Gly Asp Ala Thr Asp Thr Asp Lys Pro Glu Glu Lys
                725                 730                 735

Gln Gln Ala Asp Lys Ser Asn Glu Asn Gln Gln Pro Ser Glu Ala Ser
            740                 745                 750

Lys Glu Lys Glu Ser Asp Asp Phe Ile Asp Ser Leu Pro Asp Tyr
        755                 760                 765

Gly Leu Asp Arg Ala Thr Leu Glu Asp His Ile Asn Gln Leu Ala Gln
    770                 775                 780

Lys Ala Asn Ile Asp Pro Lys Tyr Leu Ile Phe Gln Pro Glu Gly Val
785                 790                 795                 800

Gln Phe Tyr Asn Lys Asn Gly Glu Leu Val Thr Tyr Asp Ile Lys Thr
                805                 810                 815

Leu Gln Gln Ile Asn Pro
            820

<210> SEQ ID NO 7
<211> LENGTH: 816
<212> TYPE: PRT
<213> ORGANISM: Streptococcus pneumoniae

<400> SEQUENCE: 7

Met Lys Ile Asn Lys Lys Tyr Leu Val Gly Ser Ala Ala Leu Ile
1               5                   10                  15

Leu Ser Val Cys Ser Tyr Glu Leu Gly Leu Tyr Gln Ala Arg Thr Val
            20                  25                  30

Lys Glu Asn Asn Arg Val Ser Tyr Ile Asp Gly Lys Gln Ala Thr Gln
            35                  40                  45

Lys Thr Glu Asn Leu Thr Pro Asp Glu Val Ser Lys Arg Glu Gly Ile
        50                  55                  60

Asn Ala Glu Gln Ile Val Ile Lys Ile Thr Asp Gln Gly Tyr Val Thr
65                  70                  75                  80

Ser His Gly Asp His Tyr His Tyr Tyr Asn Gly Lys Val Pro Tyr Asp
                85                  90                  95

Ala Ile Ile Ser Glu Glu Leu Leu Met Lys Asp Pro Asn Tyr Lys Leu
            100                 105                 110

Lys Asp Glu Asp Ile Val Asn Glu Val Lys Gly Gly Tyr Val Ile Lys
        115                 120                 125

Val Asp Gly Lys Tyr Tyr Val Tyr Leu Lys Asp Ala Ala His Ala Asp
    130                 135                 140

Asn Val Arg Thr Lys Glu Glu Ile Asn Arg Gln Lys Gln Glu His Ser
145                 150                 155                 160

Gln His Arg Glu Gly Gly Thr Pro Arg Asn Asp Gly Ala Val Ala Leu
                165                 170                 175

Ala Arg Ser Gln Gly Arg Tyr Thr Thr Asp Asp Gly Tyr Ile Phe Asn
            180                 185                 190

Ala Ser Asp Ile Ile Glu Asp Thr Gly Asp Ala Tyr Ile Val Pro His
        195                 200                 205

Gly Asp His Tyr His Tyr Ile Pro Lys Asn Glu Leu Ser Ala Ser Glu
    210                 215                 220

Leu Ala Ala Ala Glu Ala Phe Leu Ser Gly Arg Gly Asn Leu Ser Asn
225                 230                 235                 240

Ser Arg Thr Tyr Arg Arg Gln Asn Ser Asp Asn Thr Ser Arg Thr Asn
                245                 250                 255

Trp Val Pro Ser Val Ser Asn Pro Gly Thr Thr Asn Thr Asn Thr Ser
```

-continued

```
                    260                 265                 270
Asn Asn Ser Asn Thr Asn Ser Gln Ala Ser Gln Ser Asn Asp Ile Asp
            275                 280                 285
Ser Leu Leu Lys Gln Leu Tyr Lys Leu Pro Leu Ser Gln Arg His Val
        290                 295                 300
Glu Ser Asp Gly Leu Val Phe Asp Pro Ala Gln Ile Thr Ser Arg Thr
305                 310                 315                 320
Ala Arg Gly Val Ala Val Pro His Gly Asp His Tyr His Phe Ile Pro
                325                 330                 335
Tyr Ser Gln Met Ser Glu Leu Glu Arg Ile Ala Arg Ile Ile Pro
            340                 345                 350
Leu Arg Tyr Arg Ser Asn His Trp Val Pro Asp Ser Arg Pro Glu Gln
            355                 360                 365
Pro Ser Pro Gln Pro Thr Pro Glu Pro Ser Pro Gly Pro Gln Pro Ala
        370                 375                 380
Pro Asn Leu Lys Ile Asp Ser Asn Ser Ser Leu Val Ser Gln Leu Val
385                 390                 395                 400
Arg Lys Val Gly Glu Gly Tyr Val Phe Glu Glu Lys Gly Ile Ser Arg
                405                 410                 415
Tyr Val Phe Ala Lys Asp Leu Pro Ser Glu Thr Val Lys Asn Leu Glu
                420                 425                 430
Ser Lys Leu Ser Lys Gln Glu Ser Val Ser His Thr Leu Thr Ala Lys
            435                 440                 445
Lys Glu Asn Val Ala Pro Arg Asp Gln Glu Phe Tyr Asp Lys Ala Tyr
        450                 455                 460
Asn Leu Leu Thr Glu Ala His Lys Ala Leu Phe Glu Asn Lys Gly Arg
465                 470                 475                 480
Asn Ser Asp Phe Gln Ala Leu Asp Lys Leu Leu Glu Arg Leu Asn Asp
                485                 490                 495
Glu Ser Thr Asn Lys Glu Lys Leu Val Asp Asp Leu Leu Ala Phe Leu
            500                 505                 510
Ala Pro Ile Thr His Pro Glu Arg Leu Gly Lys Pro Asn Ser Gln Ile
        515                 520                 525
Glu Tyr Thr Glu Asp Glu Val Arg Ile Ala Gln Leu Ala Asp Lys Tyr
        530                 535                 540
Thr Thr Ser Asp Gly Tyr Ile Phe Asp Glu His Asp Ile Ile Ser Asp
545                 550                 555                 560
Glu Gly Asp Ala Tyr Val Thr Pro His Met Gly His Ser His Trp Ile
                565                 570                 575
Gly Lys Asp Ser Leu Ser Asp Lys Glu Lys Val Ala Ala Gln Ala Tyr
            580                 585                 590
Thr Lys Glu Lys Gly Ile Leu Pro Pro Ser Pro Asp Ala Asp Val Lys
        595                 600                 605
Ala Asn Pro Thr Gly Asp Ser Ala Ala Ile Tyr Asn Arg Val Lys
        610                 615                 620
Gly Glu Lys Arg Ile Pro Leu Val Arg Leu Pro Tyr Met Val Glu His
625                 630                 635                 640
Thr Val Glu Val Lys Asn Gly Asn Leu Ile Ile Pro His Lys Asp His
                645                 650                 655
Tyr His Asn Ile Lys Phe Ala Trp Phe Asp Asp His Thr Tyr Lys Ala
                660                 665                 670
Pro Asn Gly Tyr Thr Leu Glu Asp Leu Phe Ala Thr Ile Lys Tyr Tyr
            675                 680                 685
```

-continued

```
Val Glu His Pro Asp Glu Arg Pro His Ser Asn Asp Gly Trp Gly Asn
    690             695             700

Ala Ser Glu His Val Leu Gly Lys Lys Asp His Ser Glu Asp Pro Asn
705             710             715             720

Lys Asn Phe Lys Ala Asp Glu Glu Pro Val Glu Thr Pro Ala Glu
            725             730             735

Pro Glu Val Pro Gln Val Glu Thr Glu Lys Val Glu Ala Gln Leu Lys
            740             745             750

Glu Ala Glu Val Leu Leu Ala Lys Val Thr Asp Ser Ser Leu Lys Ala
        755             760             765

Asn Ala Thr Glu Thr Leu Ala Gly Leu Arg Asn Asn Leu Thr Leu Gln
    770             775             780

Ile Met Asp Asn Asn Ser Ile Met Ala Glu Ala Glu Lys Leu Leu Ala
785             790             795             800

Leu Leu Lys Gly Ser Asn Pro Ser Ser Val Ser Lys Glu Lys Ile Asn
            805             810             815
```